United States Patent
Mizutani et al.

(10) Patent No.: US 6,528,698 B2
(45) Date of Patent: Mar. 4, 2003

(54) ABSORBENT ARTICLE

(75) Inventors: Satoshi Mizutani, Kagawa (JP); Akiko Ota, Kagawa (JP); Tatsuya Tamura, Kagawa (JP)

(73) Assignee: Uni-Charm Corporation, Kawanoe (JP)

(*) Notice: Subject to any disclaimer, the term of this patent is extended or adjusted under 35 U.S.C. 154(b) by 0 days.

(21) Appl. No.: 09/883,974

(22) Filed: Jun. 19, 2001

(65) Prior Publication Data

US 2001/0053901 A1 Dec. 20, 2001

(30) Foreign Application Priority Data

Jun. 19, 2000 (JP) .................................. 2000-182876

(51) Int. Cl.[7] .............................................. A61F 13/15
(52) U.S. Cl. ....................................... 604/382; 604/372
(58) Field of Search ................................ 604/378, 381, 604/382, 385.08, 328, 385.01, 367, 372

(56) References Cited

U.S. PATENT DOCUMENTS

| | | | | |
|---|---|---|---|---|
| 3,489,148 A | * | 1/1970 | Duncan et al. | 604/365 |
| 3,559,649 A | * | 2/1971 | Grad et al. | 604/375 |
| 4,585,449 A | * | 4/1986 | Karami | 604/370 |
| 5,431,643 A | * | 7/1995 | Ouellette et al. | 604/358 |
| 5,613,962 A | * | 3/1997 | Kenmochi et al. | 604/378 |
| 5,990,377 A | * | 11/1999 | Chen et al. | 442/79 |
| 6,015,936 A | * | 1/2000 | Takai et al. | 604/358 |

FOREIGN PATENT DOCUMENTS

JP 07-328061 12/1995

* cited by examiner

Primary Examiner—Dennis Ruhl
Assistant Examiner—C L. Anderson
(74) Attorney, Agent, or Firm—Darby & Darby

(57) ABSTRACT

Provided is an absorbent article including a back sheet, an absorbent layer, and a top sheet covering at least the absorbent layer. The top sheet includes a fiber layer, and a resin layer which is applied to the surface of the fiber layer in a plurality of band-shaped rows. At least one of the rows is a discontinuous row composed of discontinuous band-shaped portions arranged at a spacing in the axial direction of the row. The area not having the resin layer between adjacent discontinuous band-shaped portions in the axial direction of the row is located at least in the region covering the absorbent layer. Accordingly, the top sheet is liquid-permeable between the adjacent rows and in the area not having the resin layer between adjacent discontinuous band-shaped portions in the axial direction of the row.

11 Claims, 6 Drawing Sheets

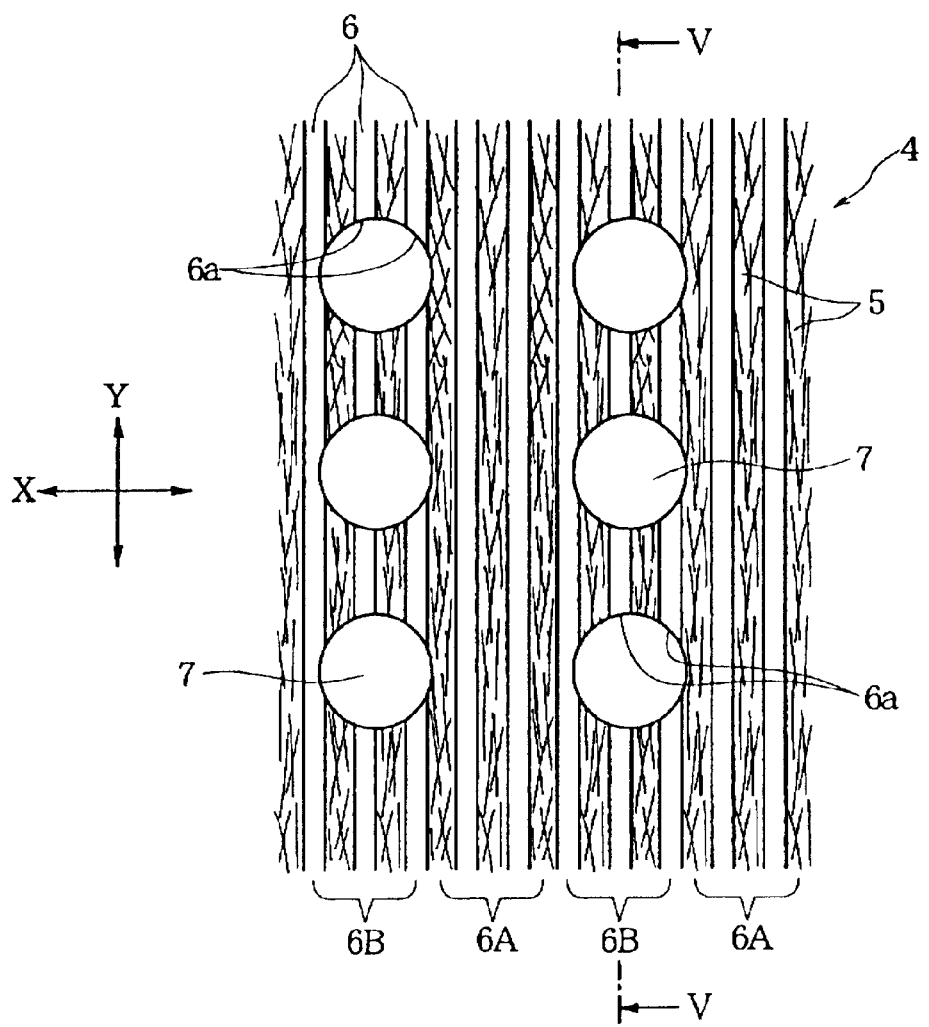

ABSORBENT ARTICLE

BACKGROUND OF THE INVENTION

1. Field of the Invention

The present invention relates generally to an absorbent article for absorbing and keeping a liquid waste such as menstrual blood and, more particularly, to an absorbent article having both functions to permeate the liquid and to prevent the liquid return, and having a high concealing (hiding) property of the menstrual blood absorbed by an absorbent layer.

2. Related Art

Conventionally, an absorbent article such as a sanitary napkin and a pantiliner is constructed to include a liquid-impermeable back sheet, a liquid-permeable top sheet and an absorbent layer sandwiched between the back sheet and the top sheet.

The liquid-permeable top sheet has used a nonwoven fabric formed of hydrophobic fibers or has been provided in a resin film with a plurality of holes for infiltrating the liquid. Alternatively, in Japanese Unexamined Patent Publication (Kokai) No. Heisei 7-328061, there is disclosed a top sheet in which the resin layer (i.e., a plastic film) is formed in a plurality of band-shaped rows in parallel at an interval on the liquid receiving side surface of a nonwoven fabric containing hydrophobic fibers.

The aforementioned structure, in which the top sheet is formed of the nonwoven fabric of the hydrophobic fibers, is excellent in that it can introduce a liquid even in a high quantity promptly into the absorbent layer. However, this structure is defective in that the top sheet tends to infiltrate the liquid having been absorbed in the absorbent layer therethrough to return it to the skin of the wearer, when the body pressure is applied to the top sheet.

On the other hand, in the structure in which the top sheet is formed of a resin film having holes, the liquid absorbed in the absorbent layer hardly returns to the skin of the wearer, and it is possible to enhance the concealing (hiding) property of making the liquid absorbed in the absorbent layer invisible from the liquid receiving side by whitening the film. However, the top sheet of the resin film tends to closely contact with the wearer's skin, thereby to provide uncomfortable feeling and make the wearer feel wet to cause the stuffiness.

If the top sheet having a resin layer, which is applied to the surface of a nonwoven fabric in a plurality of band-shaped rows is used as described in Japanese Unexamined Patent Publication (Kokai) No. Heisei 7-328061, the return of the liquid from the absorbent layer can be prevented by the band-shaped rows formed in parallel, and both the band-shaped rows of the resin layer and the nonwoven fabric can abut against the wearer's skin to reduce feeling of closely contact.

However, in order to enhance the return preventing effect of the liquid from the absorbent layer and the concealing effect of the blood absorbed in the absorbent layer, it is necessary to narrow the interval of the band-shaped rows and increase the occupied area of the band-shaped rows of the resin layer in the top sheet. However, if the interval of the band-shaped rows is excessively narrowed, the ability of the top sheet to infiltrate the liquid is degraded to avoid passing the liquid promptly.

On the other hand, the structure having the continuous band-shaped rows is inferior in the softness of the top sheet so that the top sheet provides a stiff or hard feel. Furthermore, it encounters the problem that the top sheet is hardly deformed along the protrusion of the central region covering the absorbent layer, when the central region of the absorbent article (i.e., the region covering the absorbent layer) is shaped to protrude toward the wearer's skin.

SUMMARY OF THE INVENTION

An object of the invention is to provide an absorbent article which is enabled to suppress the return of a liquid from an absorbent layer by band-shaped rows of a resin layer, which can improve the concealment of menstrual blood absorbed by the absorbent layer, which is excellent in a liquid infiltration as the entire top sheet and which can provide softness of the top sheet.

According to an aspect of the invention, an absorbent article may comprise: a back sheet; an absorbent layer; and a top sheet covering at least the absorbent layer, wherein the top sheet includes a fiber layer, and a resin layer which is applied to the surface of the fiber layer in a plurality of band-shaped rows, at least one of the rows being a discontinuous row composed of discontinuous band-shaped portions arranged at a spacing in the axial direction of the row, and the area not having the resin layer between adjacent discontinuous band-shaped portions in the axial direction of the row is located at least in the region covering the absorbent layer, so that the top sheet is liquid-permeable between the adjacent rows and in the area not having the resin layer between adjacent discontinuous band-shaped portions in the axial direction of the row.

On the other hand, some of the band-shaped rows, other than the discontinuous rows may extend continuously in the axial direction as continuous rows.

In this case, it is preferable that the continuous rows are disposed in two side regions of the absorbent article, which lie opposite one another in the transverse direction, and the discontinuous rows are disposed in a central region sandwiched between the two side regions.

On the other hand, at least one of the continuous rows may be formed between adjacent discontinuous rows.

Alternatively, only the discontinuous row may be formed on the top sheet.

In the invention having the band-shaped rows of the resin layer, it is possible to prevent the liquid having been absorbed by the absorbent layer from returning and to enhance the visual concealment of the liquid having been absorbed by the absorbent layer. Furthermore, by providing the discontinuous rows composed of the discontinuous band-shaped portions, it is possible to enhance the infiltration of the liquid thereby to infiltrate the liquid promptly. With these discontinuous band-shaped portions, the top sheet is made soft to give a smooth feel to the skin. On the other hand, the top sheet can be readily deformed along the protrusion of the central region covering the absorbent layer, when the central region of the absorbent article (i.e., the region covering the absorbent layer) is shaped to protrude toward the wearer's skin.

On the other hand, it is preferable that a hole passing through the fiber layer forming the top sheet is formed between adjacent discontinuous band-shaped portions in the axial direction of the row. With these holes being formed, it is possible to enhance the liquid infiltration function of the top sheet.

On the other hand, it is preferable that the holes have a diameter larger than the width of the discontinuous rows, and that the holes have a diameter larger than the array pitch of the discontinuous rows.

If the relation between the diameter of the holes and the width of the discontinuous rows is thus set, a part (an end) of the discontinuous band-shaped portion is extended into the inner wall portion.

When a part of the discontinuous band-shaped portion is extended into the inner wall portion of the hole, the liquid fed to the surface of the top sheet is easily introduced along the surface of the discontinuous band-shaped portions into the holes so that it can be less left on the surfaces of the band-shaped rows.

On the other hand, it is preferable that the top sheet has a portion protruding toward the absorbent layer around the edge of each hole, and a part of the discontinuous band-shaped portion is extended and fused to the fiber layer at the tip of the protruding portion.

With this construction, it is possible to increase the force of retaining the shape of the holes so that the holes are hardly crushed to be closed.

On the other hand, at least one of the discontinuous row and the continuous row has an irregular surface. In such a construction, the substantially contact area with the skin of the wearer can be reduced to avoid closely contact with the skin. On the other hand, the irregular light reflection may be caused on the surface of the discontinuous row and the continuous row to avoid the grossiness on the surface thereof.

On the other hand, it is preferable that the discontinuous rows and/or the continuous row have a width of 0.1 to 1.0 mm, and that the adjacent rows have an interval of 0.1 to 1.0 mm.

In the invention, it is possible to reduce the interval between the band-shaped rows as set forth above, prevent the liquid return from the absorbent layer, and enhance the concealment of the blood having been absorbed by the absorbent layer.

On the other hand, it is preferable for the concealment that the resin layer is whitened.

BRIEF DESCRIPTION OF THE DRAWINGS

FIG. 4 is an enlarged top plan view of an alternative embodiment of the top sheet;

DESCRIPTION OF THE PREFERRED EMBODIMENTS

Figure 1:
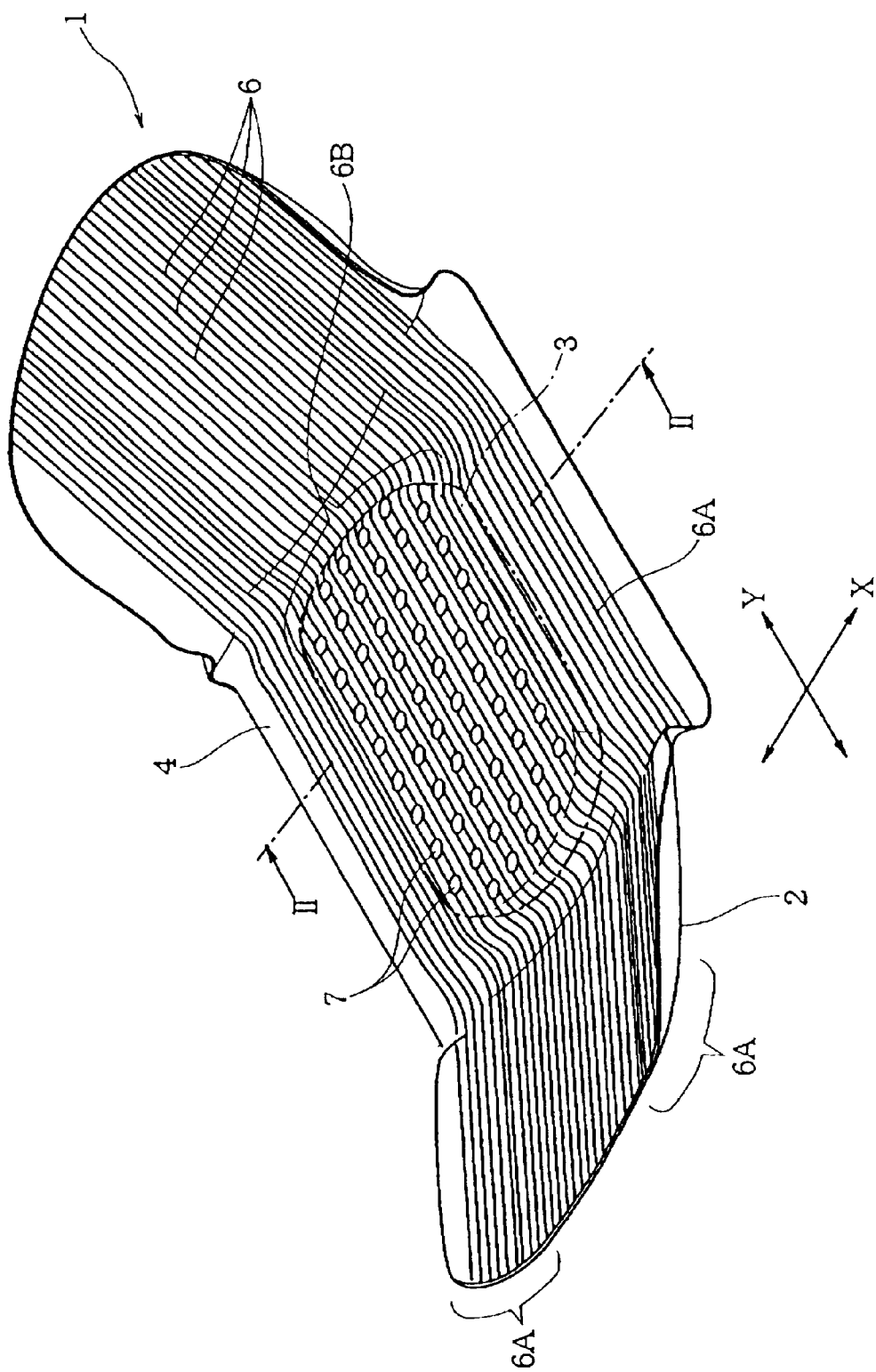
FIG. 1 is a perspective view showing a sanitary napkin as a first embodiment of an absorbent article of the invention.
Figure 2:
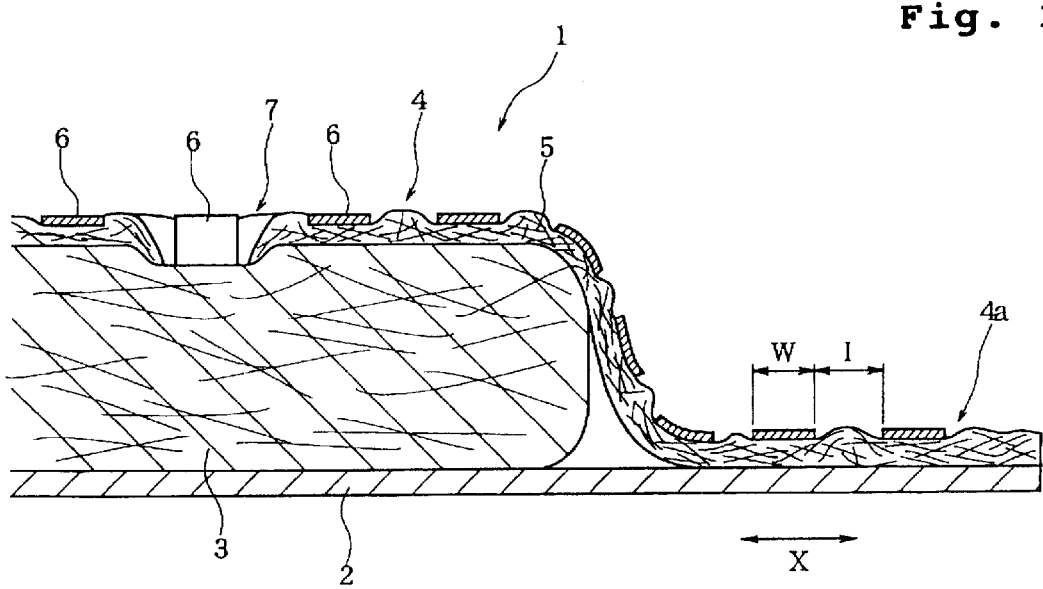
FIG. 2 is a sectional view of FIG. 1, as taken along line II—II, of the sanitary napkin shown in FIG. 1.
Figure 3:
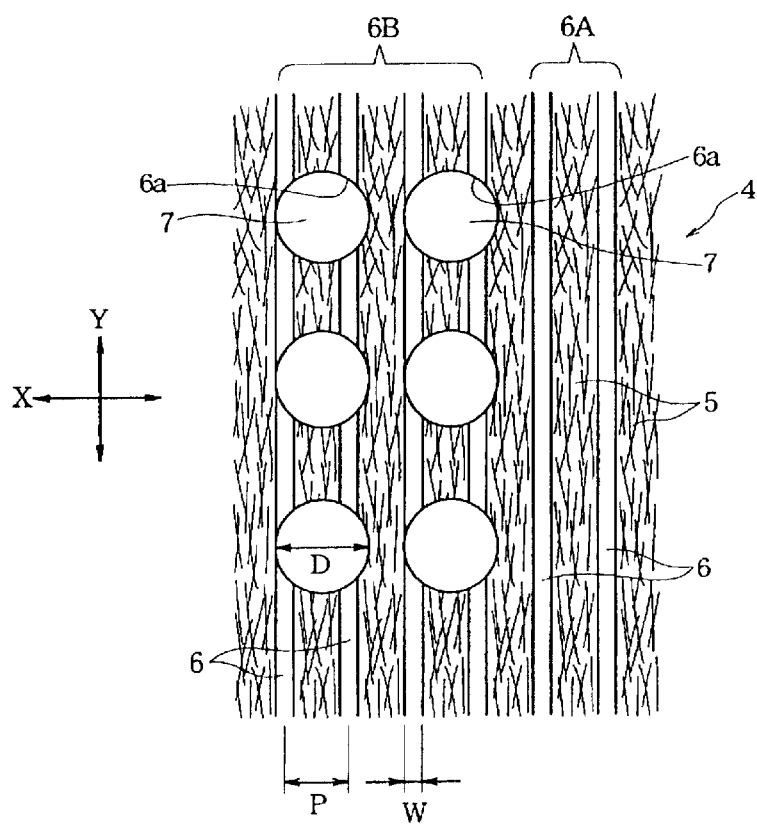
FIG. 3 is an enlarged top plan view of a top sheet.
Figure 5A:
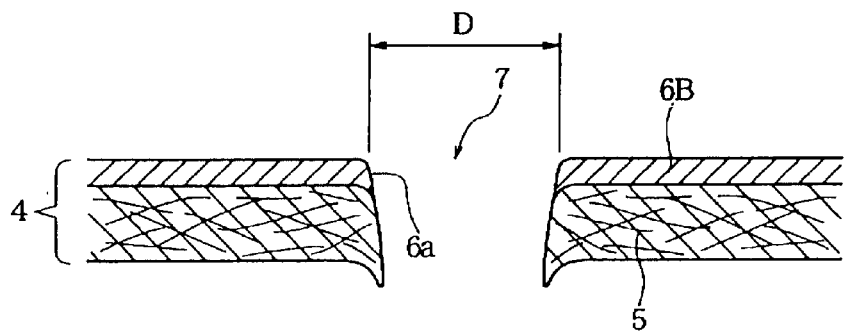
FIGS. 5A, 5B and 5C are enlarged sectional views respectively showing different embodiments of holes, as taken along line V—V of FIG. 4.
Figure 5B:
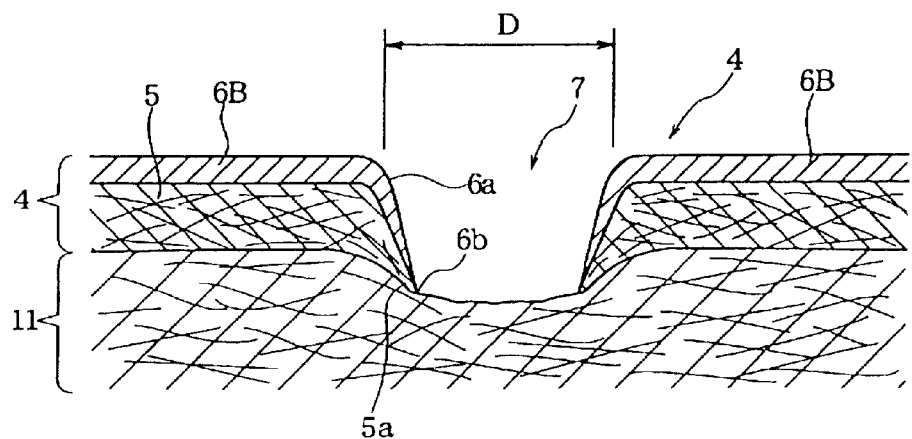
Figure 5C:
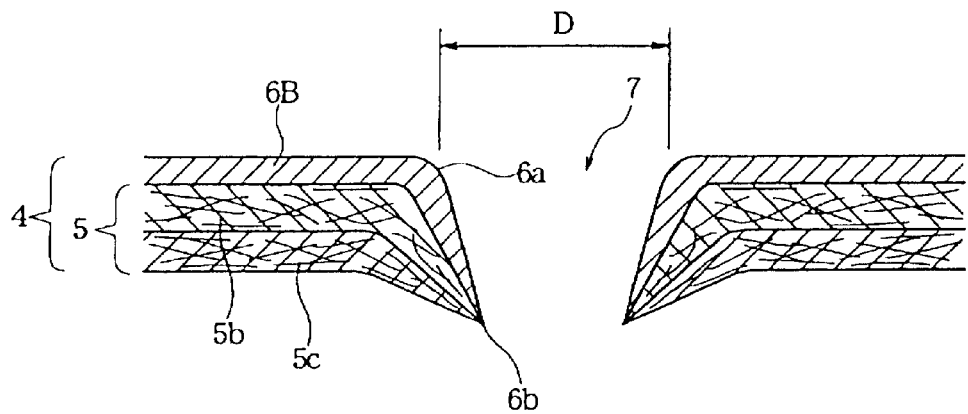

The invention will be described with reference to the accompanying drawings. FIG. 1 is a perspective view showing a sanitary napkin as a first embodiment of an absorbent article of the invention, as taken from a liquid receiving side; FIG. 2 is a sectional view of FIG. 1, as taken along line II—II; FIGS. 3 and 4 are enlarged top plan views of top sheets of the sanitary napkin, respectively showing the different embodiment; and FIGS. 5A, 5B and 5C are enlarged sectional views respectively showing the different embodiment, as taken along line V—V of FIG. 4.

The sanitary napkin 1 shown in FIGS. 1 and 2, is constructed to essentially include: a back sheet 2 to face an external support such as an underwear; an absorbent layer 3 positioned generally at the central portion of the sanitary napkin 1 and absorbing a liquid waste; and a top sheet 4 covering the liquid receiving side surface of the absorbent layer 3. In the drawings, a X direction indicates a transverse direction of the top sheet 4, and a Y direction indicates a longitudinal direction of the top sheet 4. Side edge portions 4a of the top sheet 4 in the transverse direction are joined to the surface of the back sheet 2 on both sides of the absorbent layer 3.

A resin layer 6 is applied to the liquid receiving side surface of a nonwoven fabric 5 in a plurality of band-shaped rows to form the top sheet 4. The nonwoven fabric 5 is formed of a hydrophobic synthetic fiber layer. The nonwoven fabric 5 may include a spun-bonded nonwoven fabric or a thermal bonded nonwoven fabric, and be formed of hydrophobic synthetic fibers of 2.2 to 6.6 dtexes. The hydrophobic synthetic fibers may include mono-fibers of PE (polyethylene), PP (polypropylene) or PET (polyethylene terephthalate); fibers of a graft polymer of PE and PP; or conjugated synthetic fibers of a core-sheath structure having a core of PP or PET and a sheath of PE.

The hydrophobic synthetic fibers to be employed are preferred to contain 0.5 to 10% by weight of titanium oxides so that they may be whitened to become semitransparent or opaque.

The nonwoven fabric 5 may have a structure of 100% by weight of hydrophobic synthetic fibers, but may contain about 50% by weight or less of hydrophilic fibers such as natural pulp fibers or rayon.

The nonwoven fabric 5 is preferred to have a unit weight (Metsuke) of 10 to 60 g/m$^2$ and a thickness (or bulk) of 0.3 to 10 mm.

As shown in FIG. 1, a plurality of band-shaped rows of the resin layer 6 are respectively located in parallel on the liquid receiving side surface of the nonwoven fabric 5. The respective band-shaped rows are extended in the longitudinal direction (Y-direction) at a predetermined interval in the transverse direction (the X-direction). The row has a width W of 0.1 to 1.0 mm, preferably 0.2 to 0.5 mm. On the others hand, the adjacent rows have an interval I of 0.1 to 1.0 mm, preferably 0.2 to 0.5 mm.

The resin layer 6 is made of a thermoplastic resin such as PE, PP, PET or a graft polymer of PE and PP. This thermoplastic resin is extruded by a melting extruder through a die, in which slits of the width W are linearly arranged at the interval I, onto the surface of the nonwoven fabric 5 fed in the longitudinal direction. As a result, a plurality of band-shaped rows of the resin layer 6 are formed in parallel.

On the other hand, the molten resin contains 0.5 to 10% by weight of titanium oxide so that it may be whitened to become opaque or semitransparent. Accordingly, it is possible to conceal (hide) the menstrual blood absorbed by the absorbent layer 3 visually from the liquid receiving surface side.

As shown in FIG. 1 and FIGS. 3 and 4 (FIGS. 3 and 4 respectively illustrate the different embodiment), the band-shaped rows of the resin layer 6 are composed of a continuous row 6A extending continuously in the axial direction of the row, i.e., in the longitudinal direction (the Y-direction) of the top sheet 4, and a discontinuous row 6B consisting of discontinuous band-shaped portions arranged at a spacing in the axial direction of the row. As shown in FIGS. 3 and 4, the area not having the resin layer between adjacent discontinuous band-shaped portions provides a cut-out portion 6a.

In the shown embodiments in FIGS. 3 and 4, the holes 7 are formed between adjacent discontinuous band-shaped portions in the axial direction of the row to form the cut-out portions 6a. The holes pass through the nonwoven fabric 5 and the band-shaped row of the resin layer. The discontinuous rows 6B can be formed, for example, by forming a plurality of the continuous rows of the resin layer 6 on the nonwoven fabric 5 and then piercing a plurality of the holes 7 in each continuous row by needling.

In case of forming the cut-out portions 6a in the discontinuous rows 6B, a relation of D>P holds between an array pitch P (i.e., the center distance of the adjacent discontinuous rows) in the transverse direction (the X-direction) and the diameter D (i.e., the largest internal diameter) of the holes 7, and a relation of D>W holds between the diameter D and the width W of the discontinuous rows of the resin layer 6.

The diameter D of the holes 7 is 0.5 to 2.0 mm. In the shown embodiment in FIG. 1, the holes 7 and the cut-out portions 6a are formed in the absorbent region covering the absorbent layer 3, i.e., in the central region ("the central region" is also referred to as the longitudinally and transversely central region) of the sanitary napkin 1. In other words, the holes 7 and the cut-out portions 6a are not formed in the region except for the absorbent region.

The holes 7 in the central region of the top sheet 4 have a rate of hole area (an opening area percentage) of 10 to 70%. On the other hand, the band-shaped rows of the resin layer 6 (including the continuous rows 6A and the discontinuous rows 6B) have a rate of occupied area (an occupation area percentage) of 20 to 70% relative to the entire surface area of the top sheet 4.

As shown in FIG. 3, in the central region, the continuous rows 6A are not present between the holes 7 neighboring in the X-direction (lying side-by-side in the X-direction), i.e., between the adjacent discontinuous rows 6B, so that all the band-shaped rows located in the central region may be the discontinuous rows 6B. Alternatively, as shown in FIG. 4, between the adjacent holes 7, i.e., the adjacent discontinuous rows 6B, there may be formed one, two or more continuous rows 6A having no cut-out portion 6a.

The holes 7 and the cut-out portions 6a formed in the central region as shown in FIG. 1, may be provided in the region sandwiched between two side regions of the absorbent article 1, which lie opposite one another in the transverse direction X. Alternatively, the holes 7 and the cut-out portions 6a may be provided in the whole area of the liquid receiving side surface of the sanitary napkin 1.

On the other hand, the band-shaped rows (including the continuous rows 6A and the discontinuous rows 6B) may be formed on the absorbent layer side surface (opposite to the liquid receiving surface) of the nonwoven fabric 5 forming the top sheet 4.

FIGS. 5A, 5B and 5C are enlarged sectional views showing different embodiments of the portions, in which the hole 7 is formed.

In FIG. 5A, the discontinuous band-shaped portion have edges cut by the hole 7 to form the cut-out portions 6a.

In FIG. 5B, a part (an end) of the discontinuous band-shaped portion is extended to the inner wall portion of the hole 7 of the top sheet 4, i.e., the inner hole wall portion of the nonwoven fabric 5 to form a leading end portion 6b. In the nonwoven fabric 5 around the hole 7, there is formed a protrusion 5a which protrudes toward the absorbent layer 3. At the protrusion 5a, there are thermally fused the hydrophobic synthetic fibers forming the nonwoven fabric 5 and the leading end portion 6b of the discontinuous band-shaped portion. Accordingly, the edges of the discontinuous band-shaped portions are not curled up toward the surface so that it can prevent the hole 7 from being crushed.

In the structure shown in FIG. 5B, another fiber layer 11 is sandwiched between the top sheet 4 and the absorbent layer 3. The fiber layer 11 is prepared by a hydrophilic fibers such as rayon and pulp, or a mixture of hydrophilic fibers and hydrophobic synthetic fibers.

In FIG. 5c, the nonwoven fabric 5 forming the top sheet 4 is formed of a hydrophobic synthetic fiber layer 5b and a lower fiber layer 5c. This lower fiber layer 5c is formed of hydrophilic fibers, hydrophobic synthetic fibers having a core-sheath structure of PP/PET or PE/PE and treated to be hydrophilic, or the like.

Furthermore, the hole 7 is formed through the hydrophobic synthetic fiber layer 5b and the lower fiber layer 5c. A part (an edge) of the discontinuous band-shaped portion is extended to the inner wall portion of the hole 7 to form a leading end portion 6b. The leading end portion 6b of the discontinuous band-shaped portion is joined to the hydrophobic synthetic fiber layer 5b and the lower fiber layer 5c on the side of the absorbent layer 3. If the lower fiber layer 5c is formed of the hydrophobic synthetic fibers treated to be hydrophilic, a part of the discontinuous band-shaped portion is reliably fused to the lower-fiber layer 5c.

The back sheet 2 composing the sanitary napkin 1 is formed of a liquid-impermeable sheet. This back sheet 2 is made of an air-permeable resin film, a spun-bonded or spun-laced nonwoven fabric treated to be water-repellent, or an air-permeable resin film joined to the rear surface of a nonwoven fabric. It is preferable that an adhesive layer to be adhered to an external support such as an underwear is formed on the rear surface of-the back sheet 2, and the adhesive layer is provided with a released paper for protecting the adhesive layer before the sanitary napkin is used.

The absorbent layer 3 is formed of pulverized pulp or a mixture of pulverized pulp and super absorbent polymers and is prepared by wrapping the pulverized pulp or the mixture of pulverized pulp and super absorbent polymers with an absorbent sheet of tissues or the like.

In the top sheet 4 of the sanitary napkin 1, the regions between the adjacent discontinuous rows 6B; the regions between the discontinuous row 6B and the continuous row 6A; the regions between the adjacent continuous rows 6A; and the cut-out portions 6a provide the liquid-permeable regions. When the liquid waste is fed to the top sheet 4, the liquid waste is infiltrated to the absorbent layer 3 through the nonwoven fabric 5 exposed between the adjacent rows, and further through the holes 7 serving as the cut-out portions 6a.

As shown in FIGS. 5B and 5C, if a part (an edge) of the discontinuous band-shaped portion is extended to the inner wall portion of the hole 7, the surface of the discontinuous band-shaped portion will carry out a function to introduce the liquid into the hole 7 so that the liquid fed to the top sheet 4 is promptly introduced through the hole 7 into the absorbent layer 3.

On the other hand, the resin layer 6 is applied to the surface of the top sheet 4 in a plurality of band-shaped rows (including the continuous rows 6A and the discontinuous rows 6B). Therefore, the return of the liquid to the skin of the wearer can be prevented and suppressed by the band-shaped rows so that it hardly makes the wearer feel wet. Furthermore, the top sheet 4 is provided with the discontinuous rows 6B having cut-out portions 6a to improve the liquid permeability. Also, the liquid as having been absorbed by the absorbent layer 3 is visually concealed by the band-shaped rows of the resin layer 6.

On the other hand, the top sheet 4 becomes soft, if the discontinuous rows 6B are provided on the surface of the top sheet 4. Also, the top sheet 4 becomes partially soft in the central region, if the discontinuous cut-out portions 6a are provided in the central region as shown in FIG. 1. As a result, the surface sheet 4 is felt soft by the wearer's skin. In addition, the top sheet 4 can be readily deformed along the protrusion of the central region covering the absorbent layer, when the central region of the absorbent article (i.e., the region covering the absorbent layer) is shaped to protrude toward the wearer's skin as shown in FIG. 1.

Figure 6:
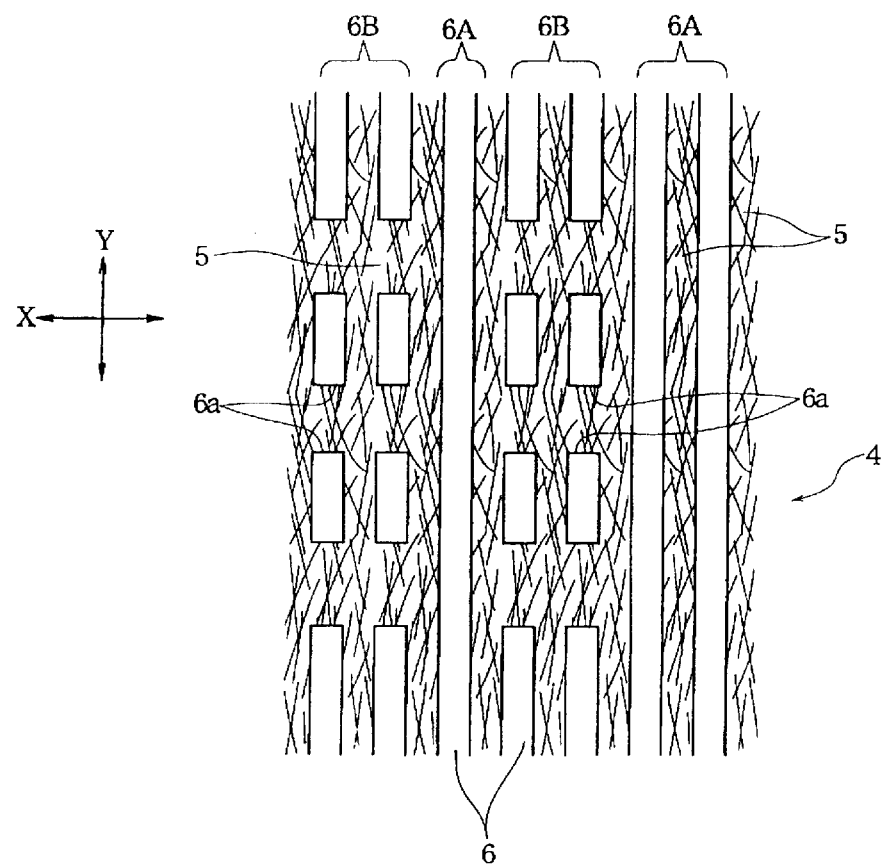
FIG. 6 is an enlarged top plan view showing a second embodiment of a top sheet.

FIG. 6 is an enlarged top plan view showing a second embodiment of a top sheet 4.

In the shown embodiment, there are formed the continuous rows 6A and the discontinuous rows 6B. In the discontinuous rows 6B, the discontinuous band-shaped portions are arranged at a spacing in the axial direction of the row. The respective discontinuous band-shaped portions have the cut-out portions 6a at both end edges thereof. No holes are formed between the adjacent discontinuous band-shaped portions. Therefore, the top sheet is permeable to liquid between the adjacent rows in the X-direction and between the adjacent discontinuous band-shaped portions (i.e., in the area of exposing the nonwoven fabric 5).

Figure 7:
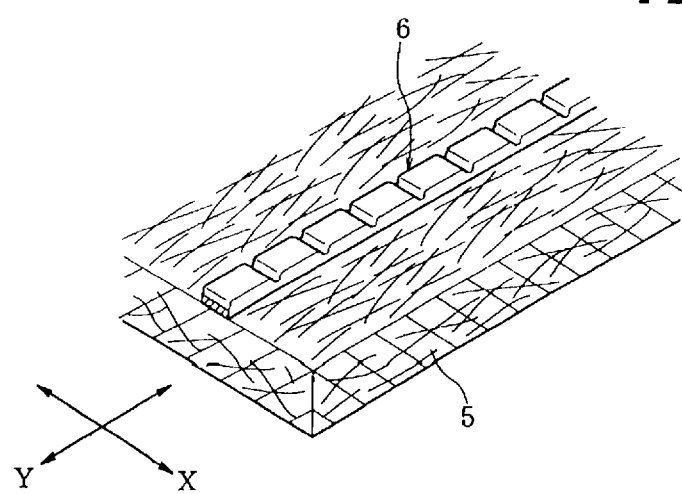
FIG. 7 is a perspective view of a resin layer having an irregular surface.
Figure 8:
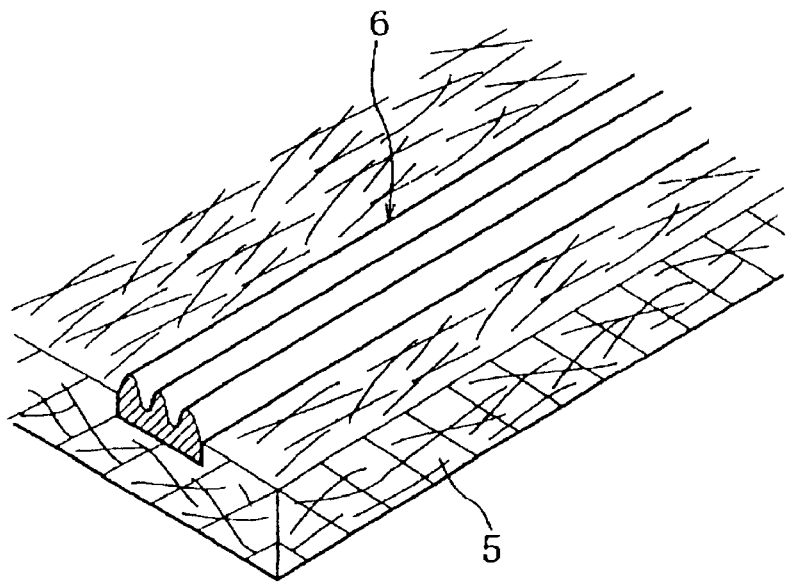
FIG. 8 is a perspective view of an alternative embodiment of the resin layer having an irregular surface.
Figure 9:
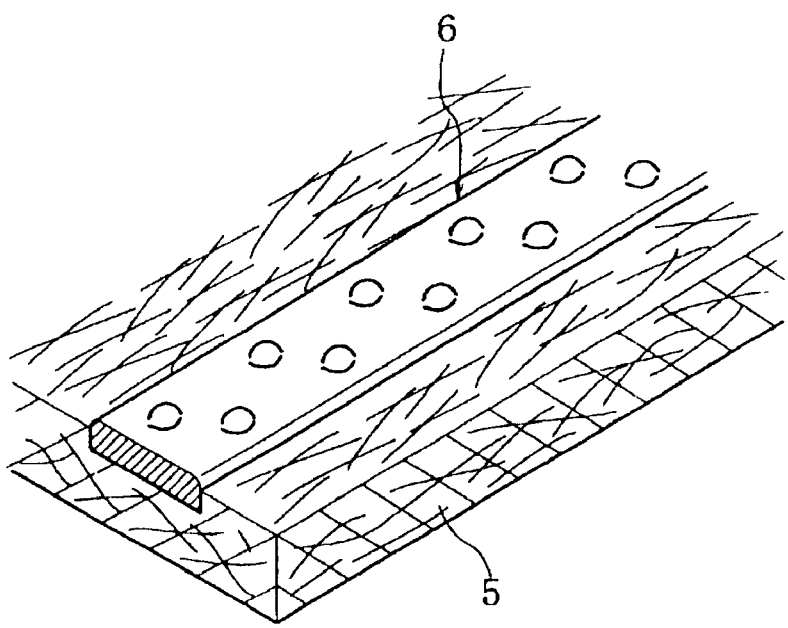
FIG. 9 is a perspective view of another alternative embodiment of the resin layer having an irregular surface.

FIGS. 7, 8 and 9 are perspective views showing a third embodiment of the invention. In the shown embodiments, the continuous rows 6A and/or the discontinuous rows 6B have irregular surfaces.

In the shown embodiment in FIG. 7, the surface of the continuous row is regularly provided with grooves to have concavo-convex portions continuing in the longitudinal direction (the Y-direction). The structure shown in FIG. 8 has a corrugated surface which is formed to have lands and the valleys respectively extending in the longitudinal direction (the Y-direction) and alternating in the transverse direction (the X-direction). The structure shown in FIG. 9 has an irregular surface which is provided with protrusions arranged regularly or irregularly.

These irregular surfaces can be formed by providing the continuous rows 6A and/or the discontinuous rows 6B on the nonwoven fabric 5, and then applying pressure thereon by a molding roll having a concavo-convex pattern, a corrugated pattern or the like.

If the continuous rows 6A and/or the discontinuous rows 6B have an irregular surface as shown in FIGS. 7, 8 and 9, the contact area with the wearer's skin can be reduced to lower the closely contact feeling of the wearer. Furthermore, with these irregular surfaces, the irregular light reflection may be caused to avoid the glossiness on the surface of the continuous rows 6A and/or the discontinuous rows 6B.

As set forth above, the absorbent article of the invention has the band-shaped rows so that it can prevent the return of the liquid and realize the visual concealment of the liquid having been absorbed by the absorbent layer. Furthermore, by providing the discontinuous rows, the area of the liquid-permeable region can be increased to infiltrate the liquid promptly. The top sheet can be made soft to enhance the deformability thereof, thereby facilitating producing.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. An absorbent article comprising:

a back sheet;

an absorbent layer; and a top sheet covering at least said absorbent layer, wherein said top sheet includes a fiber layer, and a resin layer which is applied to the surface of said fiber layer in a plurality of rectangular-shaped rows, at least one of said rectangular-shaped rows being a discontinuous row composed of discontinuous rectangular-shaped portions arranged at a spacing in an axial direction of the discontinuous row, and an area not having said resin layer between adjacent discontinuous rectangular-shaped portions in the axial direction of the discontinuous row is located at least in a region covering said absorbent layer, so that said top sheet is liquid-permeable between adjacent rows and in said area not having said resin layer between adjacent discontinuous rectangular-shaped portions in the axial direction of the discontinuous row, and some of said rectangular-shaped rows, other than said discontinuous rows extend continuously in the axial direction to provide continuous rows.

2. An absorbent article as set forth in claim 1, wherein said continuous rows are disposed in two side regions of said absorbent article, which lie opposite one another in the transverse direction, and said discontinuous rows are disposed in a central region sandwiched between the two side regions.

3. An absorbent article as set forth in claim 1, wherein at least one of said continuous rows is formed between adjacent discontinuous rows.

4. An absorbent article as set forth in claim 1, wherein said fiber layer forming said top sheet having a hole passing therethrough that is formed between adjacent discontinuous rectangular-shaped portions in the axial direction of the discontinuous row.

5. An absorbent article as set forth in claim 4, wherein said hole has a diameter larger than a width of said discontinuous row.

6. An absorbent article as set forth in claim 4, wherein said hole has a diameter larger than an array pitch of said discontinuous row.

7. An absorbent article as set forth in claim 4, wherein a part of said discontinuous rectangular-shaped portion is extended into an inner wall portion of said hole.

8. An absorbent article as set forth in claim 4, wherein said top sheet has a portion protruding toward said absorbent layer around an edge of said hole, and a part of said discontinuous rectangular-shaped portion is extended and fused to said fiber layer at a tip of the protruding portion.

9. An absorbent article as set forth in claim 1, wherein at least one of said discontinuous row and said continuous rows have an irregular surface.

10. An absorbent article as set forth in claim 1, wherein at least one of said discontinuous row and said continuous rows have a width of 0.1 to 1.0 mm, and adjacent rows have an interval of 0.1 to 1.0 mm.

11. An absorbent article as set forth in claim 1, wherein said resin layer is whitened.

* * * * *